US010376253B2

(12) United States Patent
Lederman et al.

(10) Patent No.: US 10,376,253 B2
(45) Date of Patent: Aug. 13, 2019

(54) TRANSVASCULAR AND TRANSCAMERAL DEVICE ACCESS AND CLOSURE

(71) Applicant: The United States of America, as represented by the Secretary, Department of Health and Human Services, Washington, DC (US)

(72) Inventors: Robert J. Lederman, Chevy Chase, MD (US); Ozgur Kocaturk, Rockville, MD (US)

(73) Assignee: THE UNITED STATES OF AMERICA, as represented by the Secretary, Department of Health and Human services, Washington, DC (US)

( * ) Notice: Subject to any disclaimer, the term of this patent is extended or adjusted under 35 U.S.C. 154(b) by 630 days.

(21) Appl. No.: 14/901,980

(22) PCT Filed: Nov. 27, 2013

(86) PCT No.: PCT/US2013/072344
§ 371 (c)(1),
(2) Date: Dec. 29, 2015

(87) PCT Pub. No.: WO2015/020682
PCT Pub. Date: Feb. 12, 2015

(65) Prior Publication Data
US 2016/0151056 A1    Jun. 2, 2016

Related U.S. Application Data

(60) Provisional application No. 61/863,071, filed on Aug. 7, 2013.

(51) Int. Cl.
| A61B 17/12 | (2006.01) |
| A61B 17/11 | (2006.01) |
| A61B 17/00 | (2006.01) |
| A61B 17/34 | (2006.01) |

(52) U.S. Cl.
CPC .......... *A61B 17/0057* (2013.01); *A61B 17/11* (2013.01); *A61B 17/12168* (2013.01);
(Continued)

(58) Field of Classification Search
CPC ........ A61B 2017/1205; A61B 17/0057; A61B 2017/00575; A61B 2017/00592;
(Continued)

(56) References Cited

U.S. PATENT DOCUMENTS

| 6,464,665 B1 * | 10/2002 | Heuser ................... A61B 17/11 604/101.01 |
| 2006/0224183 A1 | 10/2006 | Freudenthal |
| 2007/0208376 A1 | 9/2007 | Meng |
| 2007/0244517 A1 * | 10/2007 | Callaghan .......... A61B 17/0057 606/213 |

(Continued)

FOREIGN PATENT DOCUMENTS

| FR | 2 641 692 | 7/1990 |
| WO | WO 97/41778 | 11/1997 |
| WO | WO 00/19912 | 4/2000 |

OTHER PUBLICATIONS

European Office Action for related Application No. EP 13 812 266.8, 6 pages, dated Mar. 21, 2017.
(Continued)

*Primary Examiner* — Wade Miles
(74) *Attorney, Agent, or Firm* — Klarquist Sparkman, LLP

(57) ABSTRACT

Transcatheter methods are disclosed for introducing a large transcatheter implant or other device into an artery from an adjacent vein, for example from the inferior vena cava into the abdominal aorta. Such an access route can be formed by direct puncture through the adjoining vessels. In addition, methods and devices are also disclosed for closing arteriovenous fistulas or other cardiovascular passageways.

10 Claims, 12 Drawing Sheets

(52) U.S. Cl.
CPC .... *A61B 17/12181* (2013.01); *A61B 17/3468* (2013.01); *A61B 2017/00606* (2013.01); *A61B 2017/00641* (2013.01); *A61B 2017/1107* (2013.01); *A61B 2017/1139* (2013.01)

(58) Field of Classification Search
CPC ........... A61B 2017/00606; A61B 2017/00628; A61B 17/12168; A61B 17/12172; A61B 17/12181; A61B 17/1219; A61F 2/2427; A61F 2/243; A61F 2/2433; A61F 2/2436; A61F 2/2439
See application file for complete search history.

(56) References Cited

U.S. PATENT DOCUMENTS

| | | | |
|---|---|---|---|
| 2008/0109030 A1 | 5/2008 | Houser | |
| 2008/0195121 A1* | 8/2008 | Eldar | A61B 17/00234 606/151 |
| 2012/0046690 A1* | 2/2012 | Blom | A61B 17/0057 606/213 |
| 2013/0030521 A1 | 1/2013 | Nitzan et al. | |

OTHER PUBLICATIONS

Examination Report for related European Application No. 13 812 266.8, dated Jan. 2, 2018, 4 pages.
International Search Report and Written Opinion for related International Application No. PCT/US2013/072344, dated Jun. 16, 2014, 21 pages.

* cited by examiner

TRANSVASCULAR AND TRANSCAMERAL DEVICE ACCESS AND CLOSURE

CROSS REFERENCE TO RELATED APPLICATION

This is the U.S. National Stage of International Application No. PCT/US 2013/072344, filed Nov 27, 2013, which claims the benefit of U.S. Provisional Application No. 61/863,071,filed Aug 7, 2013. The provisional application is incorporated by reference herein its entirety.

FIELD

This application relates to devices and methods for transcatheter access between a vein and an adjacent artery, and to methods and devices for closing a fistula, access tract, or passageway through or across cardiovascular structures.

BACKGROUND

Transcatheter procedures have been a milestone advance in modern medicine. They have enabled minimally invasive procedures that reduce morbidity, improve recovery time, and permit interventions to be performed on subjects who are not otherwise candidates for surgery. Transcatheter procedures can be performed though rigid or flexible catheters. Advances in transcatheter procedures have been accompanied by challenges in developing technologies for remotely manipulating and modifying tissue and other objects within the body through the catheters. Transcatheter aortic and left heart procedures are generally performed through the femoral artery. However, femoral artery caliber or intravascular disease may preclude or complicate vascular access in a significant minority of candidates. For example, a common life-threatening risk of some transcatheter aortic heart valve procedures is vascular complications due to large introducer sheaths placed in the femoral artery.

SUMMARY

Non-surgical approaches are disclosed for introducing a large transcatheter implant or other device into the aorta via the vena cava, for example from the inferior vena cava into the abdominal aorta. An alternative access route to the abdominal aorta is provided for large-vessel introducer sheaths by direct puncture from the adjoining IVC. The iliofemoral veins are larger and more compliant than iliofemoral arteries, so that venous decompression generally averts hemorrhage in confined-space arterial perforation, and the acquired caval-aortic fistulas are not immediately life-threatening. The abdominal aorta can safely be accessed from the IVC using catheter tools, large introducer sheaths can be positioned in the aorta via the femoral vein, and persistence of the caval-aortic access tract is tolerated and can be redressed. In addition to the disclosure of the method of performing a transvascular procedure via trans-aortic introduction from the vena cava, methods and devices are also disclosed for closing other arterio-venous fistulas or other cardiovascular passageways.

Some exemplary methods disclosed herein comprise advancing a puncture device through a femoral vein to a venous crossing site located along an iliac vein or the inferior vena cava, using the puncture device to puncture a venous wall at the venous crossing site and then puncture an adjacent arterial wall at an arterial crossing site located along an iliac artery or the abdominal aorta and advancing at least a portion of the puncture device into the iliac artery or the abdominal aorta, thereby forming an access tract between the venous crossing site and the arterial crossing site, then advancing a catheter through the access tract from the venous crossing site to the arterial crossing site, and delivering the device into the iliac artery or the abdominal aorta through the catheter. The device can comprise a prosthetic heart valve, aortic endograft, left ventricular assist device, cardiopulmonary bypass device, or other cardiovascular device. The puncture device can include a guidewire and/or a needle that initially punctures the vessel walls.

The puncture device can be selectively electrically energized to puncture the venous wall and the arterial wall. In some methods, the puncture device comprises inner and outer coaxial members, wherein the inner member is advanced to initially puncture the venous and arterial walls, and the outer member is advanced over the inner member to enlarge the initial punctures and facilitate introduction of larger devices through the access tract.

Some methods further comprise advancing a target device through a peripheral artery to adjacent the arterial crossing site, and using the target device to direct the path of the puncture device through the arterial wall and into the iliac artery or the abdominal aorta.

In some methods, after the access tract is formed, a guidewire is introduced through the access tract and then the catheter is advanced over the guidewire through the access tract into the iliac artery or the abdominal aorta to deliver the device.

Some methods further comprise, after delivering the device, delivering an occlusion device over a guidewire into the access tract to close the access tract. The occlusion device can be radially compressible for transcatheter delivery and radially expandable for implantation, and the occlusion device can comprise an arterial portion for placement at the arterial crossing site, a venous portion for placement at the venous crossing site, and a neck portion for placement in the access tract. In some embodiments, the occlusion device comprises a guidewire channel extending through the venous portion, the neck portion, and the arterial portion.

Some exemplary occlusion devices disclosed herein comprise an implant comprising a venous end portion, an arterial end portion, and an intermediate neck portion between the venous end portion and the arterial end portion, wherein the implant is configured to be implanted across an arteriovenous fistula or tract connection between an artery and a vein with the arterial end portion positioned in the artery, the venous end portion positioned in the vein, and the neck portion positioned in the fistula or tract connection. When implanted, at least the arterial end portion of the implant is radially enlarged relative to the neck portion such that the arterial end portion forms an arterial skirt that contacts an endoluminal wall of the artery and blocks blood flow from the artery into the fistula or tract connection. The implant further comprises a longitudinal guidewire channel extending through the venous end portion, the neck portion, and the arterial end portion of the implant, wherein the guidewire channel allows the implant to be delivered over a guidewire and the guidewire channel is configured to be occluded when a guidewire is not present in the guidewire channel.

In some embodiments, the implant comprises a metallic shape memory material and the implant comprises a non-metallic liner on a sealing face of the radially enlarged arterial skirt that conforms to the endoluminal wall of the artery when implanted.

In some embodiments, the venous end portion of the implant is radially enlarged relative to the neck portion when the implant is implanted such that the venous end forms an enlarged venous skirt that contacts an intraluminal wall of the vein. The enlarged venous end of the implant and the enlarged arterial end of the implant can have different diameters when implanted, and can provide retention of the device between the vessels.

In some embodiments, the neck portion of the implant is longitudinally variable in length to accommodate variation in distance between the artery and the vein. In some embodiments, the neck portion of the implant is angularly articulable to accommodate non-transverse trajectories of the fistula or tract connection between the artery and the vein.

In some embodiments, the neck portion comprises a plurality of circumferential corrugations that are elastically deformable by tensile force applied on the implant to cause the corrugations to pull out and lengthen the neck portion, and in some embodiments, the neck portion comprises a woven or braided material having varying weave or braid density that allows the neck portion to lengthen under tensile force applied on the implant, and wherein the neck portion is configured to change length without substantial change in diameter.

In some embodiments, the implant comprises elastomeric material positioned in the guidewire channel that resiliently seals off of the guidewire channel when a guidewire is not present in the guidewire channel.

Some embodiments further comprise a detachable delivery system comprising an attachment member attached to a delivery shaft, wherein the attachment member is detachably couplable to the implant at an attachment location at a venous end of the guidewire channel, and wherein the delivery shaft and attachment member include a guidewire channel extending longitudinally therethrough such that the delivery system and the implant can be advanced over a guidewire extending through the guidewire channels in the delivery shaft, attachment member, and implant. The attachment member can comprise a threaded portion that screws into the attachment location of the implant and couples the guidewire channels together.

Further, the attachment member can be pivotable relative to the delivery shaft about a pivot axis that is transverse to a longitudinal axis of the delivery shaft. In some embodiments, the delivery shaft terminates in a distal ball joint having flat opposing faces and the central guidewire channel extends entirely through the delivery shaft and through the distal ball joint, and the flattened ball joint engages the attachment member such that the delivery shaft pivots in only one plane relative to the attachment member during positioning of the implant, and the delivery shaft is configured to transfer torque to the attachment member when the delivery shaft is rotated for selective attachment and detachment of the attachment member from the implant. The attachment member can have flat opposing faces between which the flat opposing faces of the distal ball joint fit, such that the pivot plane is parallel to the flat faces.

In some embodiments, the attachment member can pivot up to and/or at least about 45°, such at least about 60° or at least about 90°, from the longitudinal axis of the delivery shaft such that the attachment member and attached implant can extend across the arteriovenous fistula or tract connection at a substantially perpendicular angle from the longitudinal axis of the vein.

In some embodiments, the central guidewire channel has an ovoid shape that allows the ball joint to flex despite the presence of a semirigid guidewire inside of the channel.

In some embodiments, a recapture system can be used to recapture a deployed occlusion device. Such a recapture system can have a central guidewire lumen extending through its length such that it can be introduced over a guidewire that is positioned extending through the deployed occlusion device. The recapture system can be advanced over the guidewire until its distal end reaches the proximal end of the deployed occlusion device, whereupon the recapture system can recapture the deployed occlusion device. The recapture system may include an attachment mechanism (e.g., threads, clamp, etc.) that can attach to the proximal end of the deployed occlusion device and/or a tubular device (e.g., a sheath or catheter) that can be positioned over and/or receive the occlusion device. For example, the occlusion device can be pulled using the attachment mechanism into a sheath that causes the occlusion device to radially compress and enter into a lumen of the sheath.

Some exemplary methods of transcatheter closure of an arteriovenous fistula or adjacent openings in a vein and an artery comprise inserting a transvascular catheter housing a radially compressed occlusion device into a vein and through an arteriovenous fistula or adjacent openings in a vein and an artery, such that an end of the catheter extends into the artery, and such that the compressed occlusion device extends across the arteriovenous fistula or adjacent openings within the catheter, then retracting the catheter toward the vein such that an arterial portion of the occlusion device exits the end of the catheter and radially expands to form an enlarged arterial skirt within the artery, and with the arterial skirt positioned in the artery, further retracting the catheter such that an intermediate neck of the occlusion device exits the end of the catheter and radially expands within the arteriovenous fistula or adjacent openings, and then removing the catheter from the body and leaving the occlusion device in the body to close the arteriovenous fistula or adjacent openings.

Some methods include further retracting the catheter such that a venous portion of the occlusion device moves out of the end of the catheter and radially expands to form an enlarged venous skirt within the vein.

Some methods further comprise, prior to inserting the catheter into the vein, positioning a guidewire through the vein and across the arteriovenous fistula or adjacent openings, and then advancing the catheter loaded with the occlusion device over the guidewire into the vein and through the arteriovenous fistula or adjacent openings and into the artery, such that the guidewire passes through a central guidewire channel in the occlusion device.

In some methods, the venous end of the occlusion device is detachably coupled to a distal end of an attachment member positioned within the catheter, and the proximal end of the attachment member is pivotably coupled to a distal end of a delivery shaft within the catheter, and a guidewire channel extends through the attachment member and is coupled with the guidewire channel of the occlusion device. The method can further comprise moving the delivery shaft, attachment member, and occlusion device over a guidewire to place the occlusion device across the arteriovenous fistula or adjacent openings, and retracting the catheter over the occlusion device to allow the occlusion device to radially expand and close the arteriovenous fistula or adjacent openings. Some methods further comprise, after the occlusion device is radially expanded in the arteriovenous fistula or adjacent openings, rotating the delivery shaft to cause the attachment member to rotate and detach from the occlusion device.

In some methods, the method includes placing a buddy wire alongside the occlusion device to allow rapid recrossing of the access tract, fistula, tract connection, or adjacent openings.

Some exemplary occlusion devices for transcatheter closure of a passageway in the cardiovascular system comprise an implant that is resiliently deformable into a radially compressed configuration for transcatheter delivery and radially self-expandable to an implanted configuration, the implant comprising a proximal end portion, a distal end portion, and an intermediate neck portion between the proximal end portion and the distal end portion, the implant configured to be implanted across a passageway in the cardiovascular system with the distal end portion positioned at a first end of the passageway, the proximal end portion positioned on a second, opposite end of the passageway, and the neck portion positioned in the passageway. When implanted, the distal end portion of the implant is radially enlarged relative to the neck portion such that the distal end portion forms a distal skirt that contacts a wall of a cardiovascular chamber or vessel at the first end of the passageway and blocks blood flow from the cardiovascular chamber or vessel into the passageway, and the implant further comprises a longitudinal guidewire channel extending through the proximal end portion, the neck portion, and the distal end portion of the implant, such that the guidewire channel allows the implant to be delivered over a guidewire and the guidewire channel is configured to be occluded when a guidewire is not present in the guidewire channel.

Such occlusion devices can be configured for various different types of cardiovascular passageways, such as a transthoracic port into a heart chamber, a paravalvular leak between a prosthetic implant and a native cardiovascular structure, a ventricular septal hole or an atrial septal hole, a fistulous connection within the heart between an artery and a vein, a fistulous connection between the aorta and the heart, a coronary-cameral fistula, a passageway related to a left atrial appendage, an iatrogenic injury to the heart or a great vessel, or a hole in the heart, aorta, subclavian artery, innominate artery, iliac artery, carotid artery, superior vena cava, inferior vena cava, innominate vein, subclavian vein, iliac vein, or other great vessel. In some embodiments, the passageway is a hole through a heart wall into the heart, and the distal end portion of the implant is configured to be positioned against an inner side of the heart wall and the proximal end portion of the implant is configured to be positioned against an outer side of the heart wall, and the neck portion is configured to traverse the hole in the heart wall.

In some embodiments, the first end of the passageway is under higher pressure than the second end of the passageway and the implant comprises a compliant non-metallic liner on a sealing face of the enlarged distal skirt that conforms to the wall of the cardiovascular chamber or vessel at the higher pressure end of the passageway when implanted.

In some occlusion devices disclosed herein, the neck portion of the implant comprises at least one element that conforms to walls of the fistula, tract connection, or passageway, to obstruct blood flow through the fistula, tract connection, or passageway. The at least one element can comprise graft or elastomeric material that fills interstices in the neck portion and/or the at least one element comprises graft or elastomeric material that covers an outer perimeter of the neck portion.

In some exemplary methods, some blood is allowed to pass the deployed implant from the artery into the vein such that lower blood pressure in the vein relative to the artery decompresses the arteriovenous fistula or access tract and prevents hemorrhaging from the artery.

The foregoing and other objects, features, and advantages of the disclosed technology will become more apparent from the following detailed description, which proceeds with reference to the accompanying figures.

DETAILED DESCRIPTION

Explanation of Terms

Figure 1A:
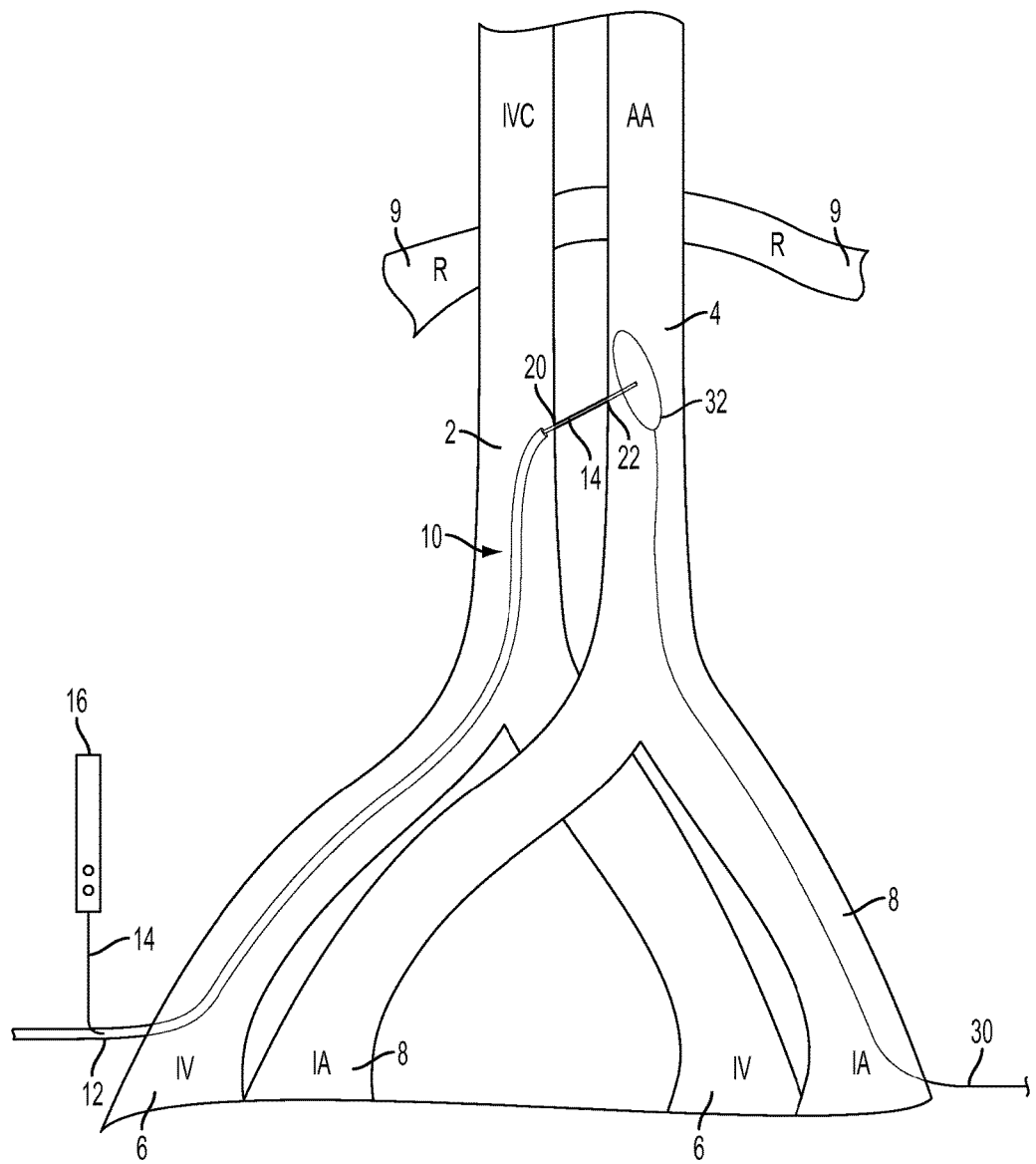
FIG. 1A shows transcatheter formation of an access tract between the inferior vena cava and the abdominal aorta.

Unless otherwise noted, technical terms are used according to conventional usage. In order to facilitate review of the various embodiments of the disclosure, the following explanation of terms is provided:

The terms "distal" and "distally" refer to a location or direction that is, or a portion of a device that when implanted (for example placed within a blood vessel) is, farther away from the point of insertion. The terms "proximal" and "proximally" refer to a location or direction that is, or a portion of a device that when implanted, or placed within the blood vessel, is closer to the point of insertion. The term "longitudinal" refers to the axis extending in the distal and proximal directions, or to the longitudinal axis of a cylindrical body or lumen.

The singular terms "a", "an", and "the" include plural referents unless context clearly indicates otherwise. The term "comprises" means "includes without limitation." The term "coupled" means physically linked and does not exclude intermediate elements between the coupled elements. The term "and/or" means any one or more of the elements listed. Thus, the term "A and/or B" means "A", "B" or "A and B."

Although methods and materials similar or equivalent to those described herein can be used in the practice or testing of the present technology, only certain suitable methods and materials are described herein. In case of conflict, the present specification, including terms, will control. In addition, the materials, methods, and devices are illustrative only and not intended to be limiting.

Exemplary Methods, Systems, and Devices

FIGS. 1A-1G show a portion of the circulatory system including the inferior vena cava ("IVC") 2, abdominal aorta ("AA") 4, iliac veins ("IV") 6, iliac arteries ("IA") 8, and renal arteries and veins ("R") 9. In some patients, characteristics of the iliac and/or femoral arteries may preclude, inhibit, or complicate transcatheter access to the aorta via the iliac arteries. For example, the iliac arteries may be diseased, calcific, obstructed, tortuous, lack elasticity, too narrow, or otherwise undesirable to for placement of large caliber aortic catheters and sheaths, such as those commonly used for delivery of a prosthetic heart valve, aortic endograft, left ventricular assist device, or cardiopulmonary bypass device. By contrast, the iliac veins can have a relatively larger caliber, greater elasticity, lower blood pressure, less obstruction, and/or can more readily allow passage of such large caliber catheters and sheaths. Alternative access sites may undesirably require surgical exposure (e.g., transapical, direct transthoracic, axillary), have percutaneous limitations, and/or constrain the intravascular working length or angle (e.g., transaortic). Thus, such devices can be introduced through an iliac vein to the IVC 2 and then across to the AA 4 via an access tract formed between the IVC and the AA, as described herein. The access tract can subsequently be closed using occlusion devices disclosed herein.

As shown in FIG. 1A, an exemplary transvascular puncture device 10 can be inserted through the IV 6 and into the IVC 10. The puncture device 10 can comprise a catheter 12 and a wire 14 within the catheter. A proximal end of the wire 14 can be coupled to an electrical power source 16, such as a unipolar electrosurgery pencil or equivalent device. The distal end of the wire 14 can then be used to create an access tract from the IVC 2 into the AA 4. For example, the power source 16 can provide an electric current through the wire 14 such that the energized distal end of the wire 14 cauterizes, cuts, burns, and/or vaporizes a hole 20 through a wall of the IVC 2 and another hole 22 through a wall of the AA 4.

The puncture device 10 can comprise the wire 14 coaxially positioned within a support wire, or wire converter, which can be positioned coaxially within the catheter 12. For example, the wire 14 can comprise a stiff-tipped guidewire, such as having a diameter of about 0.36 mm. In some embodiments, the wire 14 can optionally include a pointed or otherwise sharpened distal tip to help puncture the vessel walls. The wire converter (not shown) can have a greater diameter than the wire 14, such as about 0.89 mm. The outer catheter 12 can have a still larger diameter, such as about 5 Fr, or about 1.67 mm. The coaxial components of the puncture device 10 can be axially movable relative to each other using external proximal controls.

Prior to puncturing the wall of the IVC 2, the puncture device 10 can be configured such that the distal tip of the wire 14 protrudes distally from the other coaxial components of the device. The wire 14 can then be energized in a cutting mode using the power source 16. The cutting mode can include high current, high-duty cycle, low voltage energization of the wire 14 in order to puncture the tissue of the vessel walls. The wire 14 can be energized in discrete bursts, such as 1-2 second bursts, or continuously, while the wire 14 is advanced distally against and through the walls of the vessels. The geometry of the wire 14 can cause radiofrequency power to concentrate at its distal tip. The electrosurgical cutting can be characterized by tissue vaporization in a very local area in contact with the tip and cauterization of tissue immediately surrounding the vaporized tissue, without widespread thermal injury to surrounding tissue and without significant internal bleeding.

The location of the caval-aortic crossing can be selected in a region where the IVC 4 is relatively close to the AA 4 and in a region relatively free of obstructive vessels or other structures, such as in the abdomen between the renal arteries and the aortic bifurcation. In other embodiments, the access tract can be formed between other adjoining vessels, such as between an IV 6 and the adjoining IA 8.

To guide the crossing of the puncture device 10 into the AA 4, a transvascular target device 30 can be transfemorally inserted through the IA 8 and positioned with a loop or other target 32 in the AA 4 adjacent to a desired point of entry of the wire 14 into the AA, as shown in FIG. 1A. In other methods, the target device 30 can be introduced from other peripheral arterial access points, such as from a radial artery, a brachial artery, etc. The puncture device 10 and the target 32 can be visible within the body using known imaging techniques, such as fluoroscopy. For example, a fluoroscopic roadmap can be created from radiocontrast aortagrams to select a crossing target away from anterolateral visceral arteries and from posterolateral lumbar arteries. Using such imaging techniques, the distal tip of the wire 14 can be directed at the target 32 to guide the puncture device 10 into the AA 4.

The location of the target 32 relative to the tip of the wire 14 can confirm intraluminal positioning within the AA 4. The target device 30 can also act as a snare to capture the wire 14 can provide countertraction to help advance the puncture device 10 across the access tract if needed.

After the tip of the wire 14 has entered the AA 4, a wire convertor or other element of the device 10 positioned coaxially around the wire 14 can be advanced through the access tract over the wire 14 to increase the diameter of the access tract. Any number of such steps can be performed using sequentially larger caliber coaxial elements of the puncture device 10 to increase the size of the access tract as desired. For example, the puncture device 10 can include three or more coaxially mounted element within the catheter 12 that each have increasingly larger diameters. Any number of such coaxial element may also be configured to provide electrosurgery, as described above with reference to the wire 14, as they pass through and enlarge the access tract.

Figure 1B:
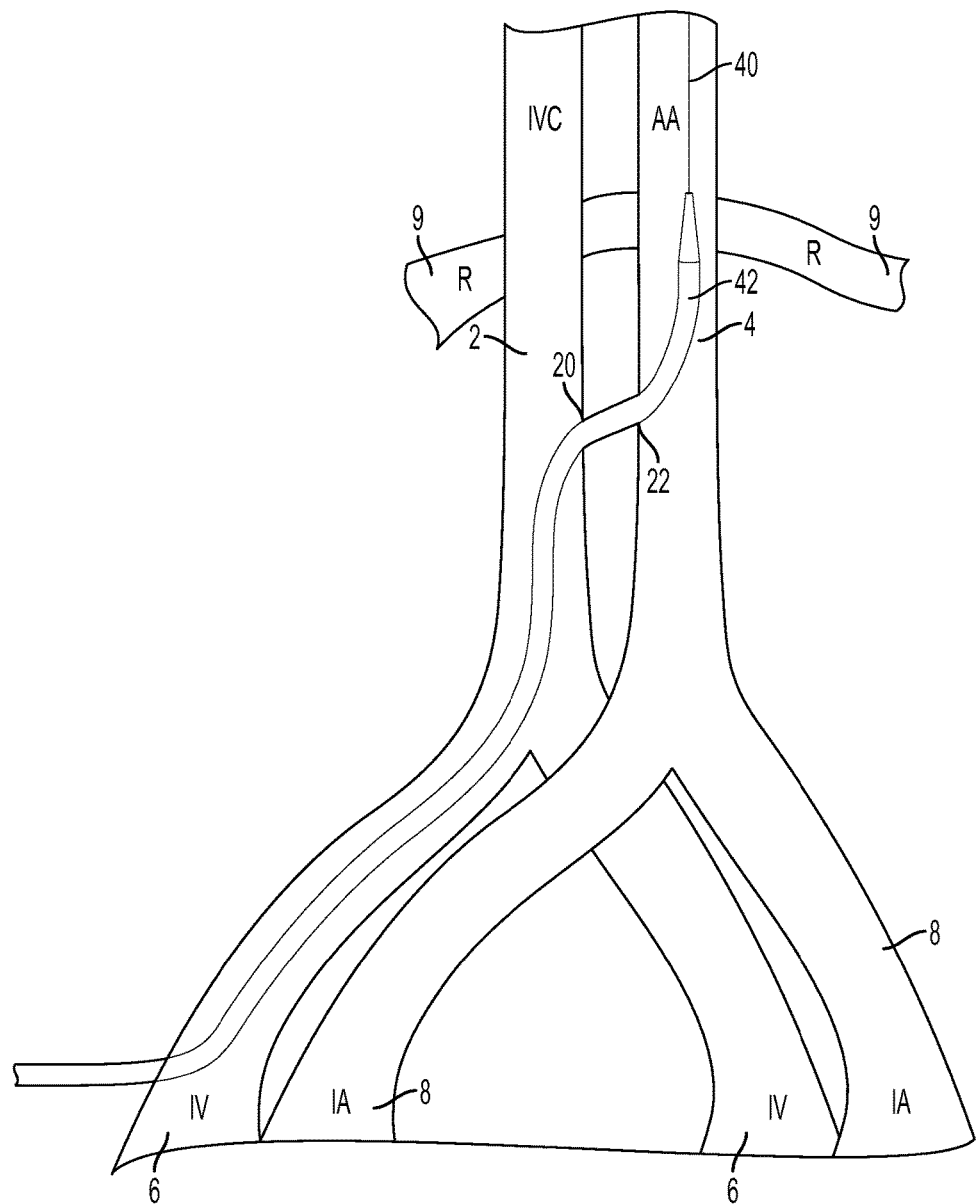
FIG. 1B shows a catheter crossing the access tract of FIG. 1A from the inferior vena cava to the abdominal aorta.

As shown in FIG. 1B, once a desired sized access tract is formed using the puncture device 10, the access tract can be used to introduce a larger caliber catheter or sheath 42 into the AA 4 for various types of transcatheter procedures. Introduction of a large caliber catheter 42 typically requires a guidewire 40 to be positioned through the access tract and into the AA 4 first, and then the catheter 42 can be advanced over the guidewire 40. In other methods, no guidewire may be needed to introduce the catheter 42.

Exemplary catheters or introducer sheaths used for caval-aortic access can be about 5-10 mm in outer diameter. The occlusion device can have a central neck size based on the outer diameter of the introducer sheath. The occlusion device may be undersized based on expected recoil of the caval-aortic fistulous tract, which has been observed in in vivo, or may be oversized to accommodate anatomic and mechanical variations in the caval-aortic fistulous tract. Ultimately, the size of the diameter of the occlusion device is desirably ±2 mm of the outer diameter of the caval-aortic introducer sheath, such as about 1 mm smaller.

In some methods, the catheter 12 can remain extending across the access tract while the wire 14 and other coaxial elements of the puncture device 10 are withdrawn through the catheter 12. Then, a new guidewire 40 can be introduced through the catheter 12 across the access tract and into the artery. The new guidewire 40 can be, for example, stiffer and/or of larger diameter relative to the wire 14. With the guidewire 40 so positioned, the catheter 12 can be retracted out of the body and off of the guidewire 40, and the larger catheter 42 carrying a cardiovascular medical device can be introduced over the guidewire 40 through the access tract to a target location in the aorta, heart, or other location.

In alternative methods, the wire 14 and/or other coaxial wire elements of the puncture device 10 can be left extending across the access tract and reused as the guidewire 40. For example, the catheter 12 can be retracted proximally over the wire 14 and/or the other coaxial wire elements within the catheter 12, leaving them to be reused as the guidewire 40 for a subsequent transcatheter procedure. In still other methods, the entire puncture device 10 can be withdrawn out of the body after the access tract is formed, and a new guidewire 40 can subsequently be introduced across the access tract.

Figure 1C:
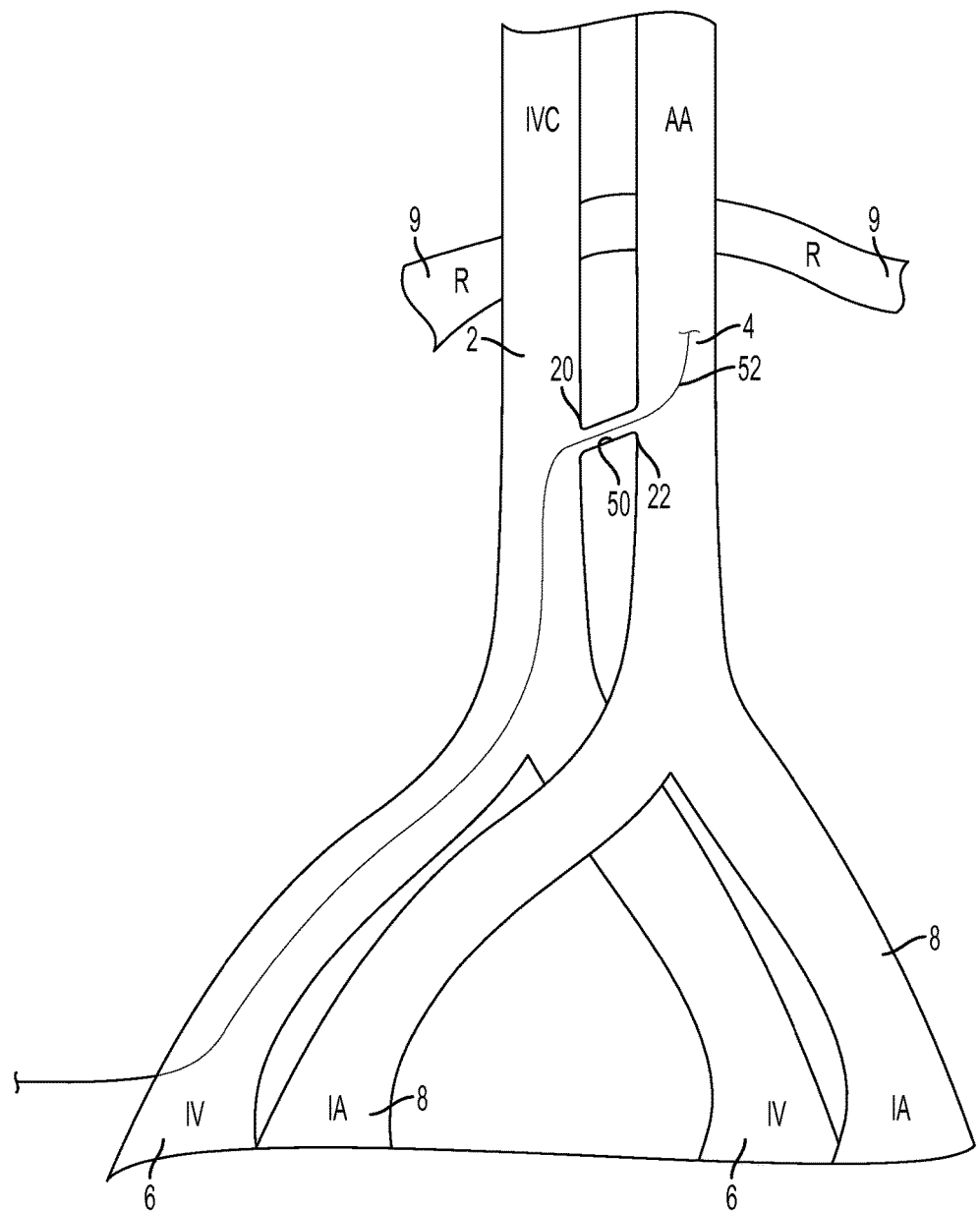
FIG. 1C shows a fistula between the inferior vena cava and the abdominal aorta after the catheter of FIG. 1B is removed.

As shown in FIG. 1C, after the procedures utilizing the catheter 42 are performed, the catheter 42 can be retracted back through the access tract. The access tract can then form a fistula, or tract connection, 50 (as illustrated) connecting the opening 20 in the vein and the opening 22 in the artery. The fistula 50 can form an enclosed fluid conduit between the adjacent vessels, and can shunt blood from the higher pressure artery to the lower pressure vein. The relatively lower pressure in the vein can decompress the fistula 50 and draw blood into the vein, reducing the likelihood of fistula rupture and/or internal hemorrhaging from the artery. In some cases, the openings 20 and 22 may not be fully connected by the fistula 50, or the openings 20 and 22 may be disconnected, allowing for some hemorrhaging, though the lower pressure in the vein encourages blood exiting the higher pressure artery to enter the vein even without the fistula 50 fully formed. Though a full fistula may not be formed between the openings 20 and 22 after withdrawal of the catheter 42, the following discussion proceeds generally under the assumption of a fistula 50 being present, as illustrated, unless otherwise described.

An unexpected feature of such methods is the apparent safety of entering and exiting the AA from the IVC without device closure of the access tract. In some cases, the access tract can recapitulate clinical spontaneous aortocaval fistula, such as is sometimes observed in ruptured abdominal aortic aneurysm. Both early and late after the catheter 42 is removed from the access tract and a fistula is formed, the fistula can easily be recrossed to deliver an occlusion device. Even in catastrophic clinical application, alternative rescue techniques are available should the deployed occlusion device fail, including endograft or open surgical repair supported if necessary by temporizing aortic balloon occlusion.

After the catheter 42 is withdrawn through the access tract and the fistula 50 is formed, it is desirable to close the fistula to prevent blood from shunting to the vein or hemorrhaging from the vessels into the abdomen. To close the fistula 50, an occlusion device can be implanted across the fistula that closes it. Described herein are various exemplary embodiments of occlusion devices, delivery systems for implanting the occlusion device, and related methods.

FIGS. 1D-1G illustrate an exemplary method of delivering an exemplary occlusion device 60 to close the fistula 50. FIGS. 1D-1G illustrate the use of the occlusion device similar to that shown in FIGS. 3-7 as an example, though other occlusion devices can alternatively be used. The occlusion device 60 can be delivered using a guidewire 52 and a catheter 54. The guidewire 52 can comprise the same guidewire 40 that was used to deliver the large caliber catheter 42, or the guidewire 52 can be a new guidewire introduced across the fistula 50. The guidewire 52 can extend through a femoral access point, through the IV 6, across the fistula 50, and into the IA 8 and/or the AA 4.

Figure 1D:
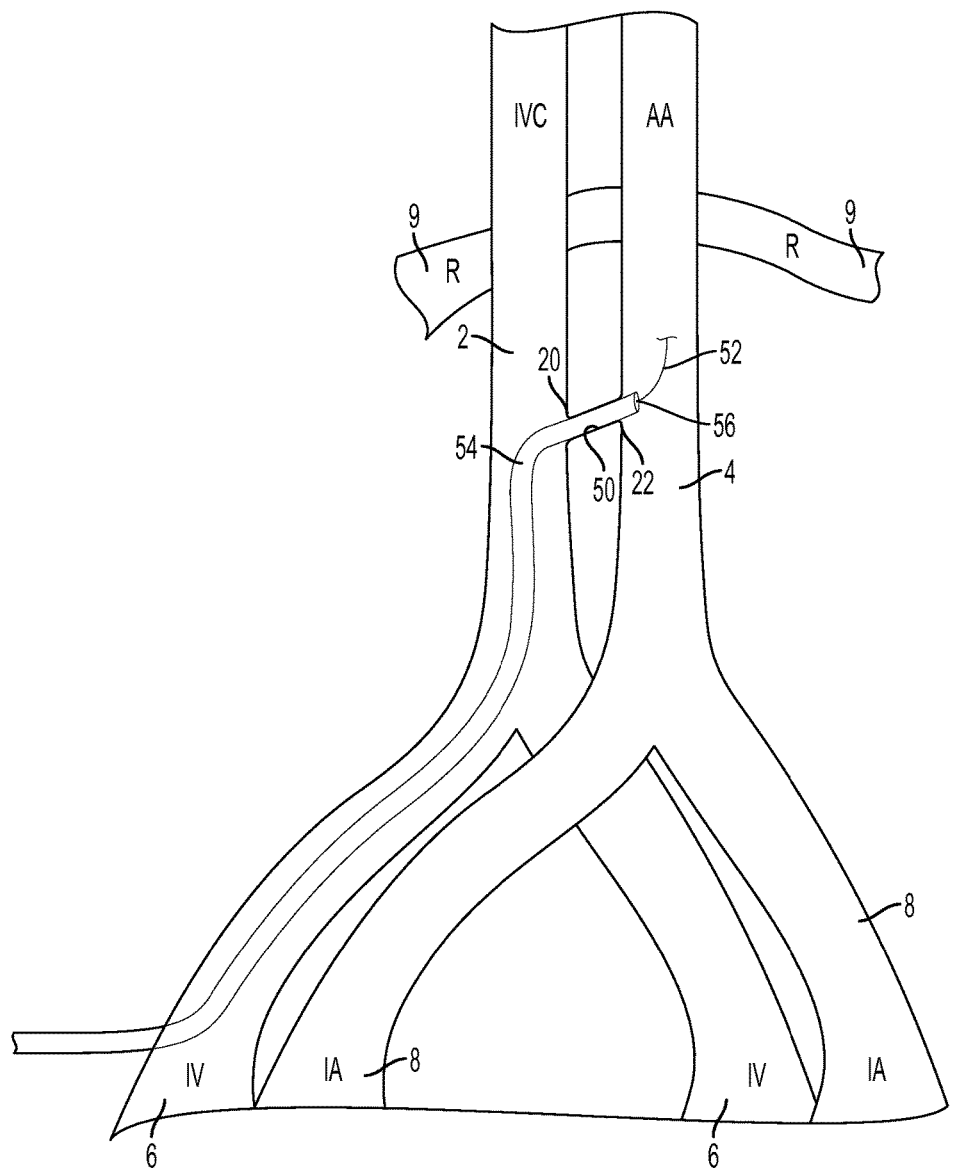
FIG. 1D shows a delivery catheter inserted across the fistula of FIG. 1C.

The catheter 54 can be advanced over the guidewire 52 such that a distal end of the catheter extends through the fistula 50, as shown in FIG. 1D. Once the catheter 54 has crossed the fistula 50, the occlusion device 60 can be advanced through the catheter 54 over the guidewire 52 and/or the catheter 54 can be retracted over the occlusion device 60 and the guidewire 52, such that a distal end, or arterial end, of the occlusion device exits the distal end 56 of the catheter, as shown in FIG. 1E.

Figure 1E:
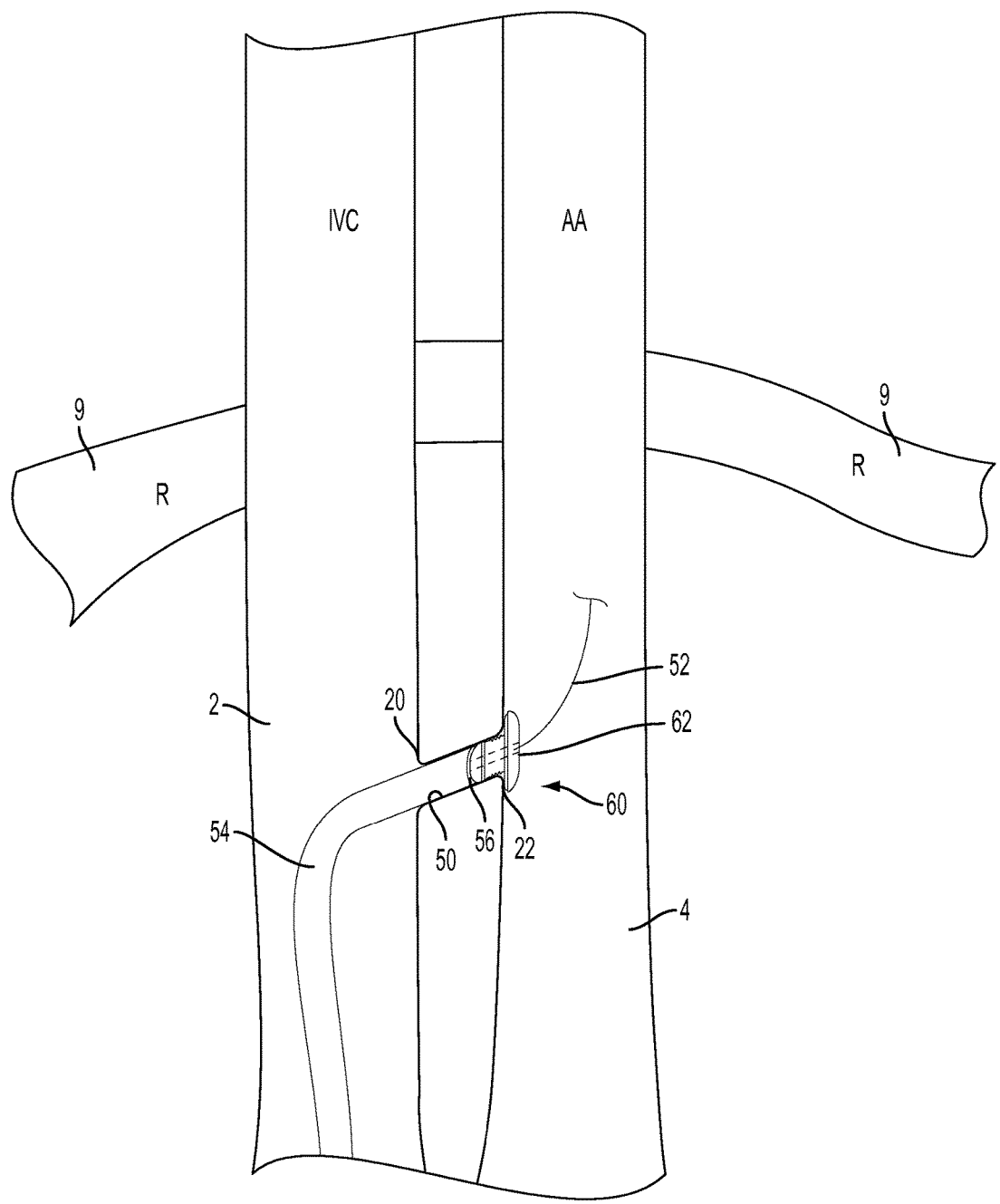
FIG. 1E shows an occluder partially deployed from the delivery catheter of FIG. 1D across the fistula.
Figure 1F:
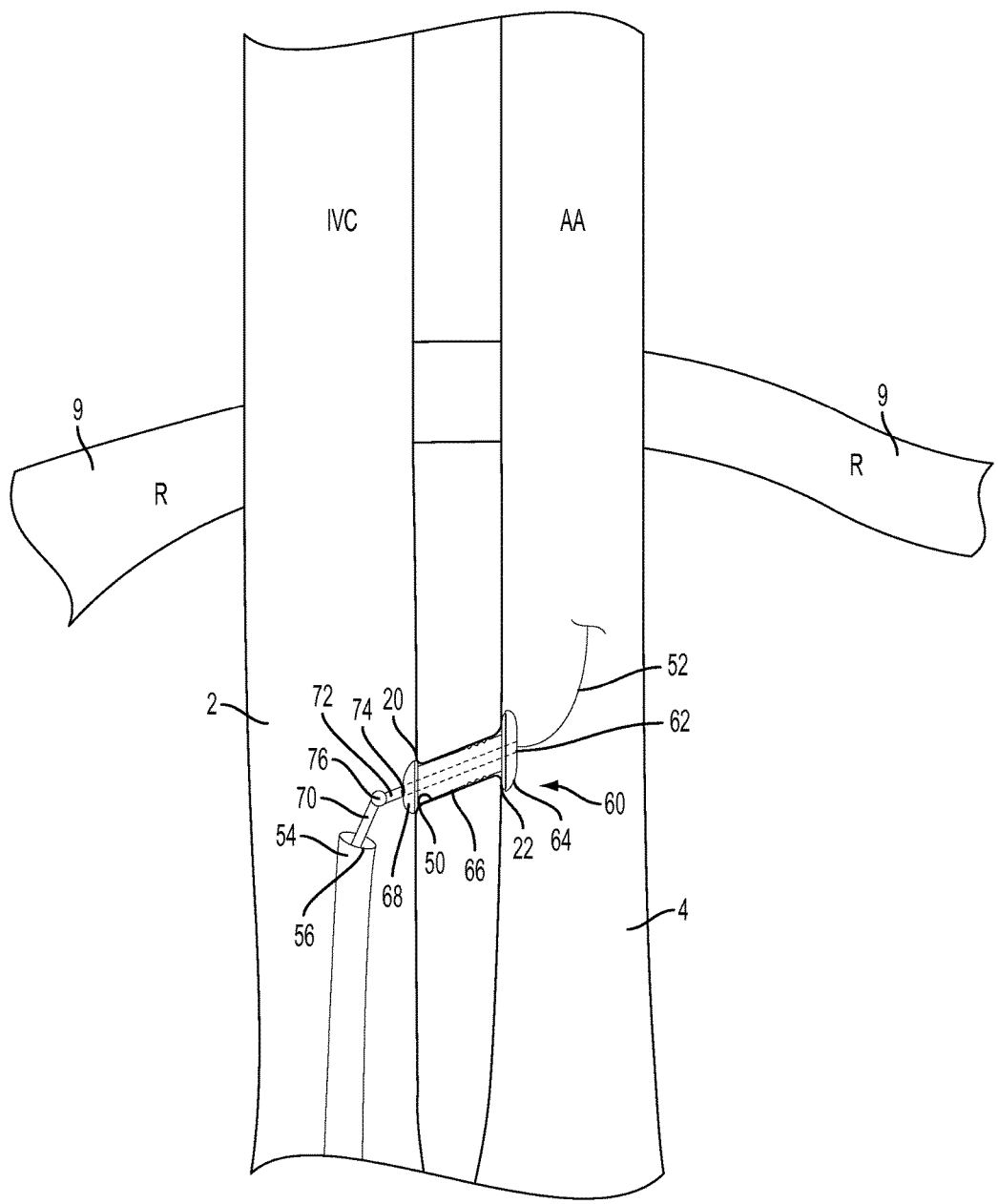
FIG. 1F shows the occluder of FIG. 1E fully deployed across the fistula, with a delivery device connected.

As shown in FIG. 1E, when the arterial end of the occlusion device 60 is freed from the catheter 54, it can resiliently expand to form a radially enlarged, disk-shaped arterial end portion 64 that contacts the endoluminal wall of the artery and helps block blood from exiting the artery through the hole 22. Further retraction of the catheter 54 over the occlusion device exposes the neck portion 66 and the venous end portion 68, as shown in FIG. 1F. The neck portion 66 can resiliently expand when freed from the catheter 54 to conform to the fistula 50 and help seal off the fistula 50. The venous end portion 68 can also resiliently expand when freed from the catheter 54 to form a disk-shaped member that contacts the endoluminal wall of the vein to help block blood from exiting the vein. The enlarged arterial and venous end portions 64, 68 can also help retain the occlusion device 60 in the fistula by preventing longitudinal motion.

As shown in FIG. 1F, delivery and placement of the occlusion device 60 in the fistula 50 can be performed using a delivery system that includes a delivery shaft 70 and attachment member 72, an example of which is illustrated in FIGS. 8-12 as delivery shaft 400 and attachment member 300. The delivery shaft 70 in FIG. 1F is coupled at a distal end to the proximal end of the attachment member 72, with a pivotable joint 76 therebetween. The distal end of the attachment member 72 is releasable attached to an attachment site 74 at the venous end of the occlusion device 60. The guidewire 52 passes longitudinally through a guidewire channel 62 in the occlusion device, through a corresponding guidewire channel extending longitudinally through the attachment member 72, through the pivot joint 76, and through the delivery shaft 70. Because the guidewire 52 passes through all of the components, they can be advanced over and be guided by the guidewire within the delivery catheter 54 to the fistula location.

The pivot joint 76 can allow the shaft 70 and the attachment element 72 to pivot up to or at least about 45°, such as at least about 60°, or at least about 90°, such that the occlusion device 60 can be inserted across the fistula 50 at an angle from the longitudinal axis of the delivery shaft 70 and the longitudinal direction of the vein.

Figure 1G:
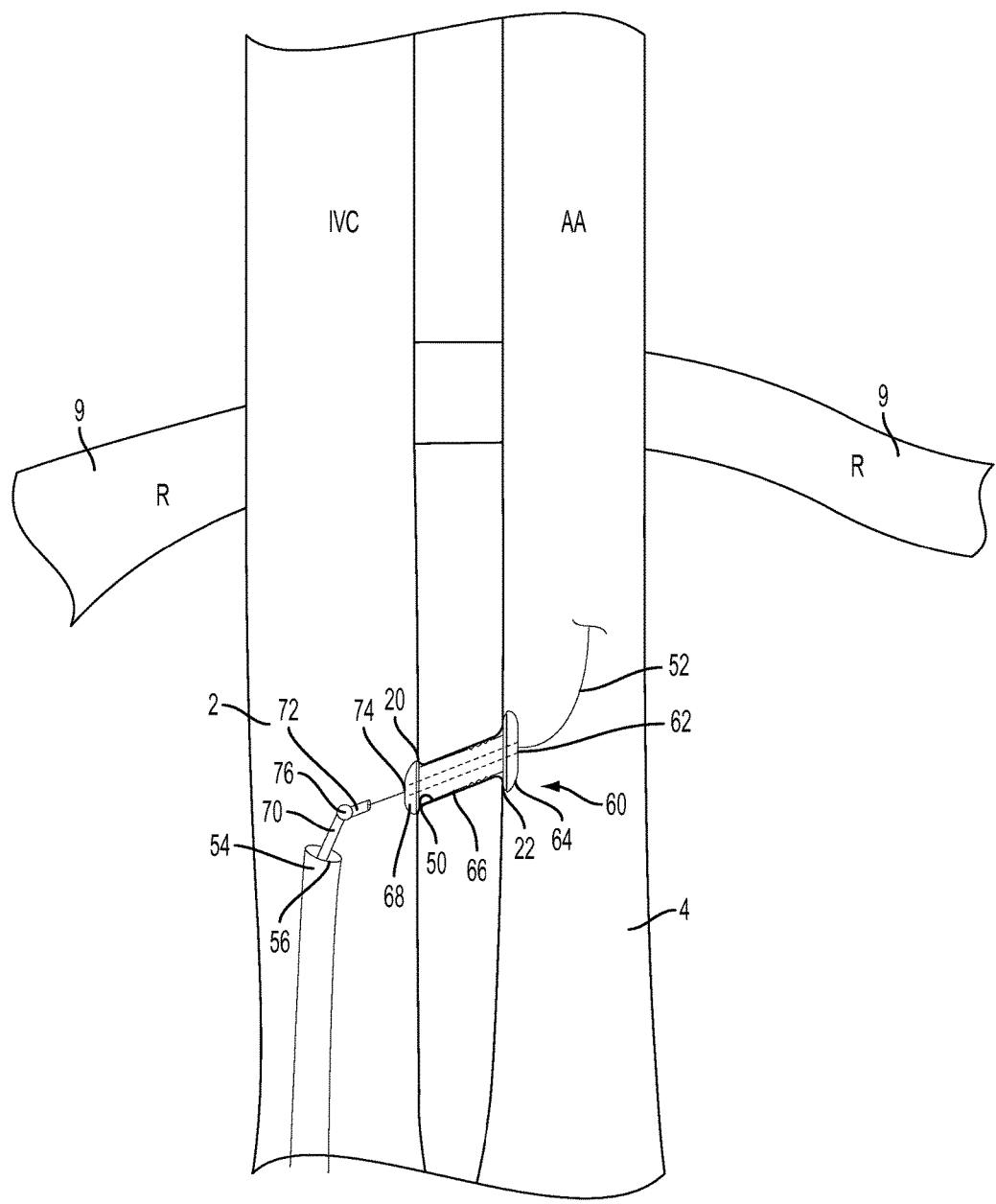
FIG. 1G shows the occluder of FIG. 1E fully deployed across the fistula, with the delivery device disconnected.

As shown in FIG. 1G, once the occlusion device 60 is implanted, the attachment member 72 can be disconnected from the venous end portion 68 and retracted. To disconnect, the delivery shaft 70 can be rotated, which imparts a torque across the pivot joint 76 to the attachment member 72, which causes the attachment member to disconnect from the occlusion device 60, such as by unscrewing from the occlusion device 60.

The guidewire 52 can also be retracted through the device 60 and out of the body. As the guidewire 52 passes out of the guidewire channel 62 in the occlusion device, the guidewire channel 62 can become occluded to block blood flow through it.

In some methods disclosed herein, a buddy wire can be left alongside the occlusion device 60 during closure, which can facilitate repositioning and/or removal of the deployed occlusion device. The buddy wire allows rapid re-crossing of the passageway.

Figure 2:
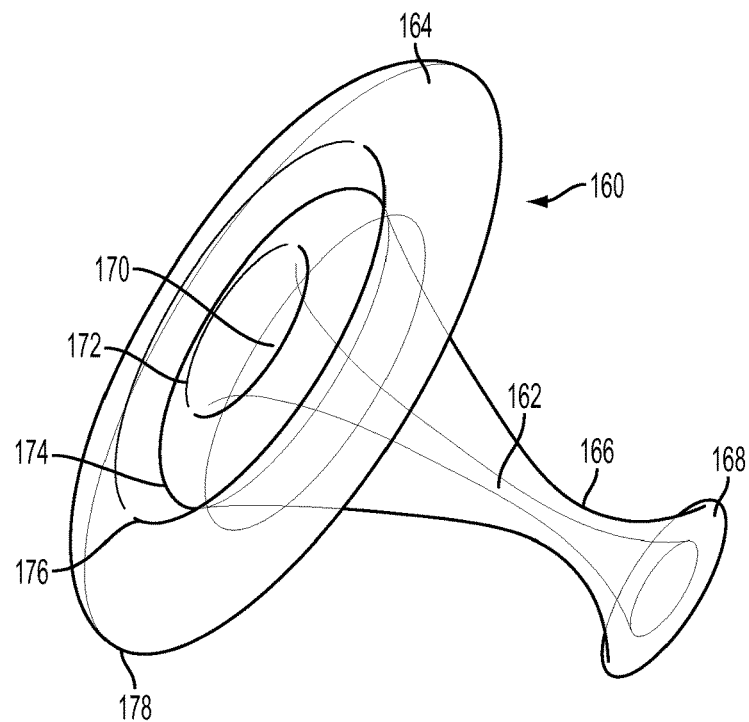
FIG. 2 illustrates an exemplary occluder that can be advanced over a guidewire through a catheter to close an arteriovenous fistula.

FIG. 2 illustrate an exemplary occlusion device 160 and FIGS. 3-7 illustrate another exemplary occlusion device 260. The delivery devices 160, 260, and other embodiments described herein can be used in the methods shown and described with relation to FIGS. 1A-1G, or for various other uses. Occlusion devices described herein can also be used to close various other passageways or holes in the cardiovascular system. Exemplary passageways of holes that can be closed with the described occlusion devices include, but are not limited to, other arteriovenous fistulas or tract connections, a ventricular septal hole or an atrial septal hole (congenital or otherwise), a transthoracic port into a heart chamber, such as through the heart apex into a ventricle, a paravalvular leak between a prosthetic implant and a native cardiovascular structure, such as between a prosthetic heart valve an the native valve orifice, a fistulous connection within the heart between an artery and a vein, a fistulous connection between the aorta and a heart chamber, a coronary-cameral fistula, a passageway related to a left atrial appendage, an iatrogenic injury to the heart or a great vessel, or a hole in the heart wall, aorta, subclavian artery, innominate artery, iliac artery, carotid artery, superior vena cava, inferior vena cava, innominate vein, subclavian vein, iliac vein, or other great vessel.

The occlusion devices disclosed herein can comprise a resiliently deformable material that allows the devices to be radially compressed for transcatheter delivery and allows the devices to resiliently self-expand to an operative configuration when released from the delivery catheter. In some embodiments, the occlusion device can comprise a shape-memory metal having superelastic properties, such as nitinol, flexinol, titanium-palladium, platinum alloys, etc. In some embodiments, the shape-memory material can comprise woven or braided strands of thin wires that form a mesh-like material. For example, the embodiment 260 of FIGS. 3-7 illustrates such a mesh-like material.

Often, when using the disclosed occlusion devices to close a cardiovascular passageway, the passageway has a first end that is under higher pressure relative to the second opposite end. For example, with a transthoracic port created through a heart wall, the end of the port within a heart chamber is under higher pressure than the end of the port outside the heart. Due to this pressure differential, blood tends to flow through the passageway from the first end toward the second end of the passageway. Further, the lower pressure end of the passageway can draw blood into the lower pressure region, which decompresses the passageway.

Some occlusion device embodiments disclosed herein include a first end portion that is configured to be located at the higher pressure first end of the passageway, and a second end portion that is configured to be located at the lower pressure second end of the passageway. For example, the first ends 164 and 264 of the devices 160 and 260, respectively, are configured to be located at the higher pressure end of a passageway. The first end portion can comprise a disk-shaped body that is radially enlarged relative to an intermediate neck portion. The first end portion can include a sealing material or surface (e.g., the sealing material 280 of the device 260) that contacts tissue around the first end of the passageway and helps seal against the tissue to restrict blood from flowing out of the higher pressure chamber or vessel between the occlusion device and the native tissue. In some embodiments, the sealing surface of the first end portion can comprise gasket-like qualities, such as being pliant, elastomeric, and/or resiliently deformable to conform to the native tissue wall around the first end of the passageway.

In some embodiments, such as the device 160 in FIG. 2, the first end portion 164 can have an undulating end surface, such as annular ridges, e.g., 172 and 176, and annular valleys, e.g., 170 and 174. Further the peripheral rim 178 of the first end portion can be curved or tapered toward the second end portion moving radially outward to help the rim 178 seal against the intraluminal wall of the artery while providing minimal hemodynamic resistance to blood flowing past the first end portion in the artery.

The mesh-like material of the occlusion device can be substantially blood-impervious when the device is implanted in the expanded configuration, such that blood is substantially prevented from passing through the first end portion or through other walls of the device. In some embodiments, some of the walls of the occlusion device can also comprise a graft material or polymeric material lining the surface of the mesh and/or filing interstices of the mesh to enhance the blood-impervious nature of the mesh walls. This can also promote immediate sealing and healing and promote tissue ingrowth to secure the device over time.

The shape memory frame of the occlusion device may not necessarily conform to irregularities of the endoluminal walls and fistula tract. For example, aortic atheromata and calcific plaques can create irregular anatomic surfaces to which the frame may not conform, which can in turn inhibit immediate hemostasis and allow some continued aortic bleeding. This problem can optionally be addressed by coating the outer surface of the occluder frame with coatings that interact with the underlying anatomic substrate to achieve improved hemostasis. For example, the outer surface of the neck and/or enlarged ends of the occluder can be coated with an elastomeric material that achieves improved conformity between the surface of the occluder and the anatomic substrate. Alternatively, a cylindrical "bag" on the outside of the neck portion of the device can be filled with silicon or solidifying material in order to enhance apposition of the device with the endoluminal wall surface and the fistula tract and therefore to improve hemostasis, while allowing the neck portion to more freely lengthen independently of the bag.

Examples of materials that can be applied to the surfaces of the occlusion device to enhance sealing and/or promote biocompatibility, including the sealing material 280 at the first end portion, can include polyetherketoneketone (PEKK), dacron, silicone, polyester, polyethylene, polypropylene, supramid, parylene and polydimethylsiloxane. An elastic polymer, such as silicone, polyester or polyethylene, can coat any portion of the occluder frame or the entire frame.

The neck portion of the occlusion device (e.g., neck portion 166 of device 160 and neck portion 266 of device 260) can expand within the passageway and help seal the passageway. In some embodiments, the neck portion can expand to conform to the contours of the passageway to help close off gaps between the outside of the neck portion and the walls within the passageway. The neck portion can have a generally cylindrical shape, such as neck portion 266 in FIG. 3, or can have non-cylindrical and/or variable diameter shapes, such as in the neck portion 166 of FIG. 2 that has an hourglass shape with conical sections meeting at their apexes. In some embodiments, the neck portion can comprise an compliant outer liner, such as of a graft material or polymeric material, that can resiliently deform and conform to the contours of the passageway, and thereby immediately restrict blood that gets past first end portion from traveling through the passageway around the outside of the neck portion.

The guidewire channel 162, 262 through the occlusion device can include an elastomeric material, such as silicone, silicone rubber, ultra high molecular weight polyethylene. The elastomeric material can permit the device to slide along the guidewire, but when the guidewire is removed the elastomeric material expands to occlude the lumen of the device to prevent flow of blood through the lumen. An intrinsically elastic polymer that forms the inner face or core of the guidewire lumen can radially expand toward the longitudinal axis of the guidewire lumen to close the central lumen after the guidewire is removed. The elastic core can be, for example, an elastomeric cylinder placed within the guidewire lumen that permits independent movement of the neck frame. For example, the neck frame can be selectively lengthened independently of the elastomeric cylinder in such embodiments.

In some embodiments, the neck portion of the occlusion device can be adjustable in length. For example, the neck portion 266 comprises a corrugated portion 282 that can lengthen and shorten to adjust the length of the neck and the distance between the first and second end portions 264, 268. The corrugated portion 282 can be configured to maintain a substantially constant diameter as it changes in length to help maintain a seal between the outer surface of the neck portion and the inner walls of the passageway. In some embodiments, each of the corrugations of the corrugated portion 282 can selectively expand one at a time when the neck portion is under tension. The corrugated portion 282 can be resiliently biased to return to a contracted configuration wherein the neck portion is at a shortest length. Such biasing of the neck portion can provide residual tension between the first and second end portions that help the first and second end portions clamp together across the passageway.

When an occlusion device with an adjustable length neck portion is deployed, the first end portion can be positioned against a wall around the first end of the passageway and then the second end portion of the device can be pulled longitudinally away from the first end portion to apply tension on the neck portion, which can selectively cause the corrugations to pull out one at a time until the neck portion is at a desired length corresponding to the length of the passageway. Then, the second end portion can be radially expanded to contact the tissue around the second end of the passageway. A resilient tension in the neck portion due to a shortening bias in the corrugated portion can cause the first and second end portions to clamp together and seal the passageway.

In other embodiments, the neck portion can be adjustable in length due to a variable weave or braid in the mesh having variable weave or braid density, which can allow the neck portion to resiliently stretch in length without changing its diameter. Such embodiments can also provide a shortening bias that imparts a residual tension between the first and second end portions when implanted.

In embodiments with a neck portion that is adjustable in length, the device can be able to self-adjust to accommodate variation in the length of the passageway after the device is implanted. For example, when an occlusion device is used to close a non-connected gap between an opening in a vein and an opening in an adjoining artery (e.g., where no fistula has formed to bridge the openings), the vein and the artery can move relative to each other and change the length of the gap or passageway. A variable length neck occlusion device can be implanted across such a gap to close the adjoining openings in the vein and artery, with the first end portion positioned in the artery against an endoluminal wall of the artery and the second end portion positioned in the vein against an endoluminal wall of the vein, and the neck portion extending through the two adjoining wall openings and spanning between the vessels. As the vein and the artery move relative to each other and the gap length varies, the neck portion of the occlusion device can correspondingly lengthen and shorten. When the vessels move apart, the vessels can apply a tension on the first and second end portions, causing the neck portion to resiliently lengthen, and when the vessels move closer together, the tension is released, causing the neck portion to resiliently shorten back toward its natural shorter configuration.

In some embodiments, the corrugations or other extendible elements in the neck portion can be formed by variable braiding or weaving of the shape-memory metal strands. The expandable portion of the neck can have a denser braiding or weaving, enforced by compression during annealing that would allow the neck to be lengthened by applying longitudinal tension, yet without narrowing. This dense braiding can be applied to a selectable longitudinal fraction of the length of the neck. For example, the neck can allow lengthening between 0-100% of the unconstrained length, between 50-100% of the unconstrained length, or other amounts.

In some embodiments, the neck portion can also be adjustable and/or deformable in non-longitudinal directions. For example, the neck portion can allow the first end portion to move relative to the second end portion in a plane perpendicular to the longitudinal direction of the neck portion. The neck portion can skew, bend, curve, and/or articulate to accommodate such non-longitudinal motion between the end portions. For example, when implanted across an arteriovenous fistula that is not perpendicular to the longitudinal axis of the adjoining vessels (like the fistula 50 in FIGS. 1C-1G), the neck portion can distort or skew to allow the first and second end portions to be displaced along the longitudinal direction of the adjoining vessels. In FIG. 1G, for example, the first end portion 64 is positioned superior to the second end portion 68, and the neck portion 66 extends at an angle of about 20° from horizontal between the end portions. At the same time, the end portions 64, 68 can maintain a flush contact with the generally parallel vertical endoluminal walls of the vessels because the neck portion is distorted or skewed while the end portions are shifted off-axis from each other. This distortability of the neck portion advantageously can allow the end portions to shift off-axis from each other while maintaining a generally parallel relationship between their respective sealing surfaces, which allows the end portions to form tight seals against the endoluminal wall despite an angled or non-transverse trajectory between the opening in the two vessels, as shown in FIG. 1G. Such an angled or non-transverse access tract can be desirable when formed for purposes of providing transcatheter access between the vessels, as in FIGS. 1A-1B.

Disclosed embodiments of the occlusion device can lengthen, shorten, and/or skew off axis without compromising or changing its diameter of the guidewire channel passing through the device. This can be achieved, for example, by physically separating an inner polymeric or graft material within the guidewire channel from the shape-memory mesh frame. In such embodiments, the shape-memory mesh frame can be capable of moving separately from the compliant material in the guidewire channel that extends through the neck. Similarly, compliant material on the outer surfaces of the shape-memory mesh frame (particularly the neck) can provides hemostatic occlusion but still allow lengthening or distortion of the neck to accommodate the variable lengths and trajectories of different passageways. In such embodiments the pliant outer sealing material can be capable of stretching to accommodate changes in the length or shape of the neck.

The longitudinal adjustability and non-longitudinal adjustability/distortability of the neck portion, as described above, can also help the occlusion device maintain seals at the end portions and bridge the passageway while the adjoining vessels move relative to each other in the longitudinal directions of the vessels, causing the trajectory angle between the end portions of the passageway to vary. Thus, the adjustability of the neck portion can allow the occlusion device to be used in cardiovascular passageways of many different configurations, providing a very versatile occlusion device.

For the caval-aortic access methods disclosed herein, a typical entry site into the infrarenal aorta is midway between the renal arteries and the aorto-iliac bifurcation, on the right lateral wall of the aorta and the left lateral wall of the cava. The specific site can be chosen to help avoid calcification that may increase the difficulty of crossing. There are not usually any critical structures interposed between the aorta and cava. The typical horizontal distance between the infrarenal abdominal aorta and inferior vena cava in adults is about 3-15 mm. This distance may lengthen as the hypotenuse of the triangle when the crossing angle varies from purely transverse to the vessels. The selectively variable length of the occlusion device assures that the entire caval-aortic fistulous tract or passageway is occupied by the device, and that the caval and aortic skirts do not protrude excessively into the cava and aorta lumens respectively.

The second end portion of the device (e.g., end portion 168 or 268) can radially expand to a diameter greater than the neck portion to help secure the occlusion device within the passageway. In some embodiments, the second end portion can also seal against tissue around the second end of the passageway to block blood flow therebetween, while in other embodiments, sealing at the second end portion may not be needed or desirable.

In embodiments where sealing at the second end is desired, the second end portion can be configured similar to the first end portion, having an enlarged body with an optional sealing material facing the first end portion to help seal against the tissue around the second end of the passageway. The diameter of the second end portion can be about the same as the diameter of the first end portion, or the second end portion can be substantially smaller in diameter than the first end portion, as shown in FIGS. 2-7.

The configuration of the second end portion can depend on the type of passageway it is intended to be used in. Consequently, certain occlusion device configuration may not be desirable for closing certain types of passageways, while other occlusion device configurations may be versatile enough to be used in many different types of passageways. Generally, however, sealing at the second end portion can be less important than sealing at the first end portion because the blood pressure at the first end portion is typically greater, and because in some cases it is acceptable and/or desirable for blood that gets past the first end portions to be allowed to escape past the second end portion into the lower pressure region.

Using the caval-aortic fistula 50 of FIG. 1C as an example, the pressure in the AA 4 is much greater than the pressure in the IVC 2, and thus sealing at the first end portion within the AA 4 is desired to restrict that amount of blood that passes across into the IVC 2 without having circulated through the body. However, it can also be desirable to allow any blood that does pass the first end portion in the AA 4 to vacate the fistula 50 into the IVC 2 in order to decompress the fistula and reduce the risk of rupturing the fistula 50 and/or having internal hemorrhaging in the body between the vessels. Thus, the second end portion in the IVC 2 can be configured to provide retention of the device in the fistula 50 without sealing, or with less sealing relative to the sealing between the first end portion and the AA 2. Even though it may be desirable to let blood from the AA 4 that enters the fistula 50 escape into the IVC around the second end portion, it may still be necessary to prevent blood from the IVC from escaping into the fistula, such as if the fistula is ruptured or otherwise not completely formed and/or if the seal between the first end portion and the AA is substantially complete and little or no blood from the AA passes into the fistula.

If a fistula is not formed between openings in adjoining vein and artery, or only partially formed, or ruptured, it can be more desirable to provide substantial sealing between the second end portion and the vein to prevent blood from hemorrhaging from the vein into the open region between the vessels. In this situation, there can be little or no pressure in the fistula or open region between the vessels to keep blood in the vein from escaping. Further, in such a case, substantially complete sealing between the first end portion and the artery can be needed, as there is reduced ability for arterial blood passing the first end portion to enter the vein and recirculate safely.

For a passageway through the heart apex into the left ventricle, as another example, the pressure inside the left ventricle is much greater than the pressure outside the heart, and consequently blood strongly wants to flow through the opening out of the heart. Unlike an arteriovenous fistula, in this situation it is very undesirable to let blood pass through the passageway, and thus substantially complete sealing at the first end portion within the left atrium is desirable. In case some blood does pass the first end portion, sealing by the neck portion in the passageway can also be desirable to further reduce the risk of blood escaping the heart. However, sealing may not be needed at the second end portion in such a passageway. The high pressure differential can urge the first end portion of the device against the inner wall of the left atrium and at the same time urge the second end portion away from the outer wall of the heart. This urging can keep the device in place in the opening even without traction from a second end portion. The urging of the first end portion against the ventricular wall can also strengthen the seal there, with the sealing between the neck portion and the passageway providing a second line hemostatic bather, and making sealing at the second end portion unnecessary. Further, because there is no native blood outside the heart, there is no need to block blood from passing the second end portion into the passageway. Also, the lack of pressure outside the heart limits the amount of sealing the device can provide at the second end portion to depend on the residual tension in the neck portion tending to clamp the two end portions together. In this situation, an occlusion device with no second end portion, or a minimal second end portion, can be used, though the presence of a second end portion may not cause any negative effects.

The occlusion devices disclosed herein can comprise a central guidewire passageway extending longitudinally through the first end portion, through the neck portion, and through the second end portion. For example, the device 160 of FIG. 2 includes a guidewire passageway 162 and the device 260 of FIGS. 3-7 includes a guidewire passageway 262. The guidewire passageway allows the device to be introduce into the body over a guidewire, which can guide and control the delivery and deployment of the device. In addition, the guidewire channel allows the occlusion device to be more readily recovered, repositioned, or withdrawn and replaced if maldeployed.

The guidewire passageway through the occlusion device can be configured to occlude when a guidewire is not present in the passageway, to block blood from passing through. In some embodiments, the resilient nature of the shape-memory mesh material of the occlusion device can cause the guidewire passageway to close upon removal of the guidewire. In some embodiments, an elastomeric material or other resilient material can be positioned in the guidewire passageway that tends to expand and seal off the guidewire passageway when the guidewire is not present. In some embodiments, the occlusion device does not include a central guidewire channel, and the device is not delivered over a guidewire. For example, the delivery catheter 12 can house a compressed occlusion device and be advanced to the deployment passageway without the assistance of a guidewire.

Figure 3:
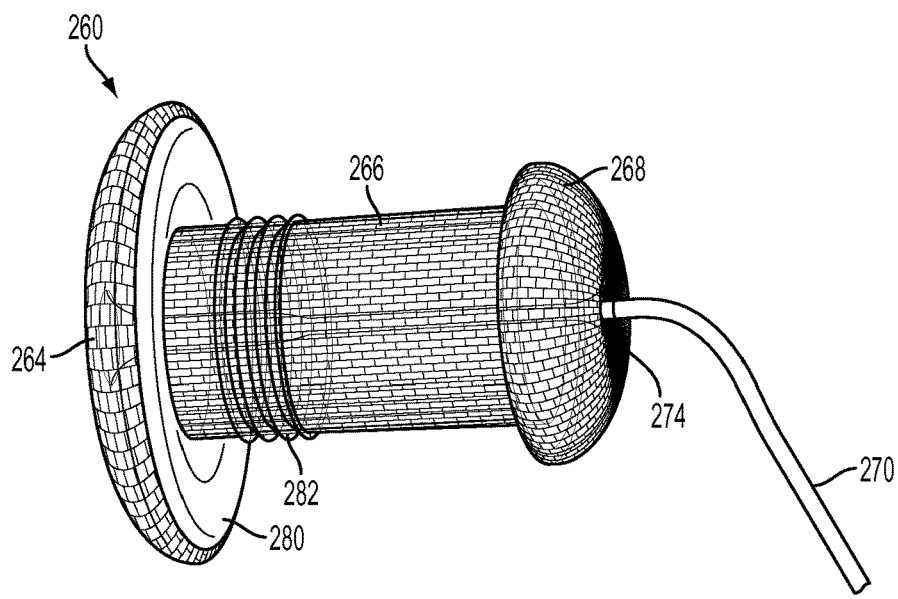
FIGS. 3-7 illustrates another exemplary occluder that can be advanced over a guidewire through a catheter to close an arteriovenous fistula.
Figure 4:
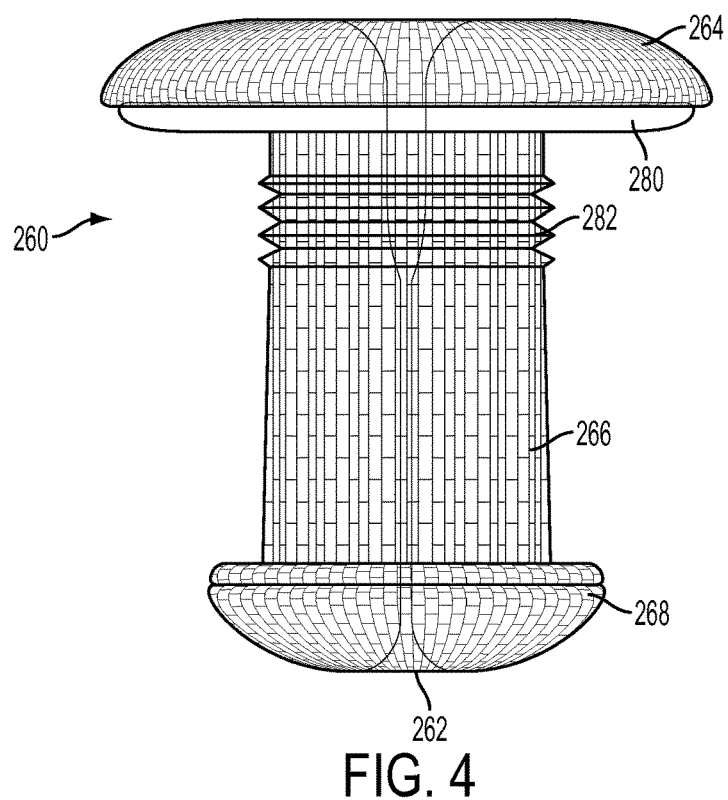
Figure 5:
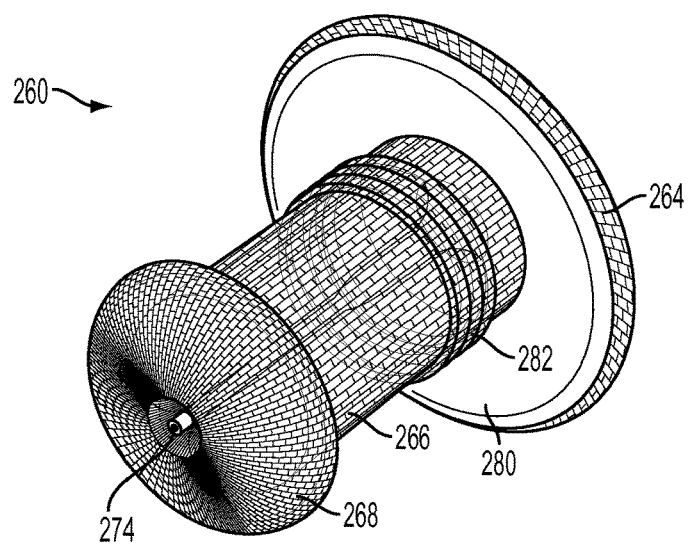
Figure 6:
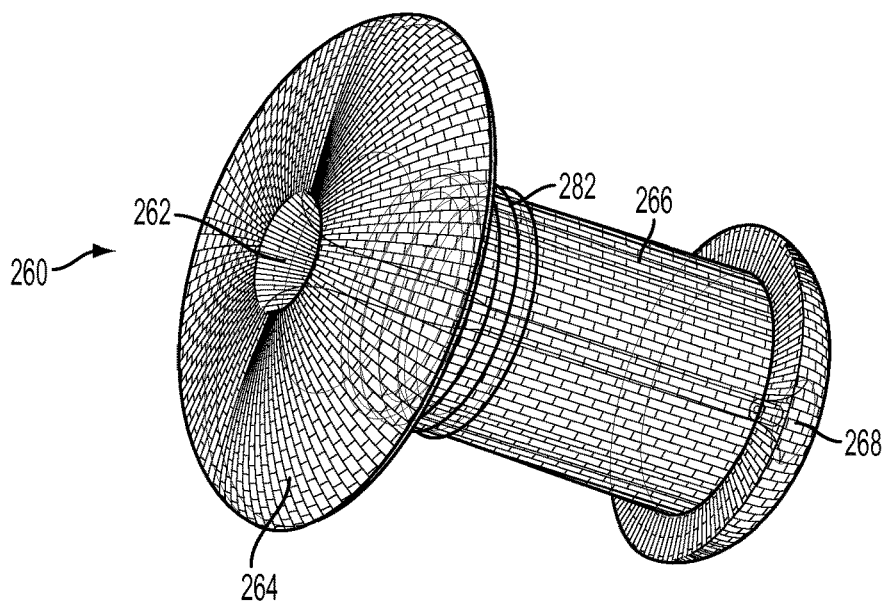
Figure 7:
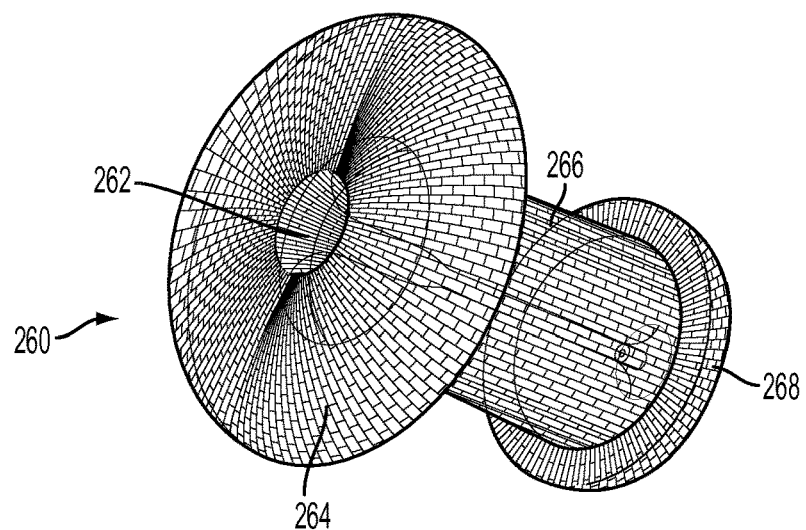
Figure 8:
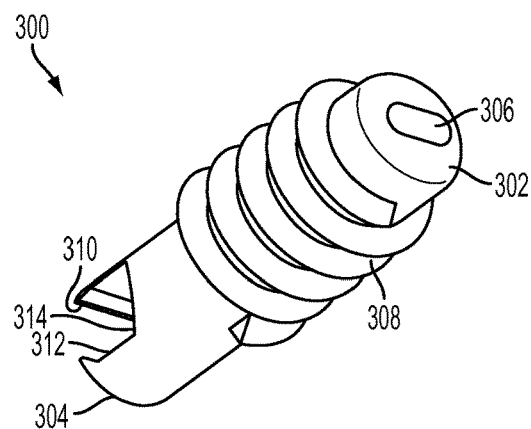
FIGS. 8-12 illustrate a delivery device for an occluder.
Figure 9:
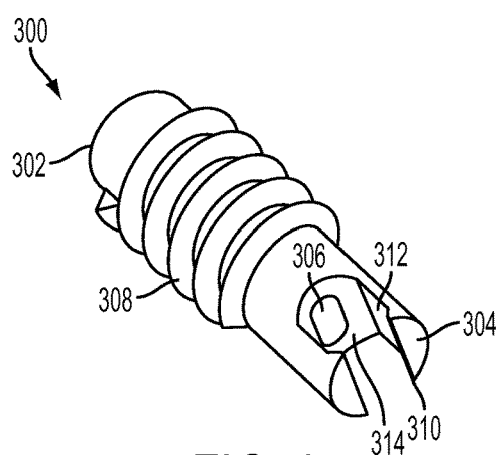
Figure 10:
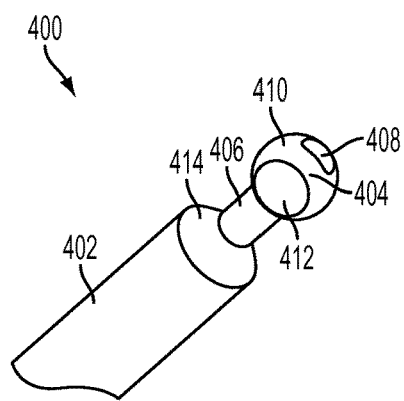

As exemplified in FIGS. 3 and 5, some occlusion devices can have an attachment location 274 at the second end 268 of the device that is configured to selectively attach to and detach from a delivery system 270. The attachment location 274 can be at the end of the guidewire channel 262. In some embodiments, the attachment location is threaded to allow the delivery system 270 to screw onto and unscrew from the occlusion device. In other embodiments, other types of coupling mechanisms can be used.

In some embodiments, the occlusion devices disclosed herein can include one or more anchoring mechanisms to secure the occluder in its intended anatomic location. For example, such anchoring mechanisms can comprise spiral fixation devices, tines, shaped curved barbs, or other protrusions that extend from the occluder and penetrate the wall of the passageway or walls of the vessels or chambers, or mechanisms that wrap around adjoining vessels or chambers in order to secure fixation of the occlusion device.

Methods for delivering disclosed occlusion devices to passageways in the heart, for example, can include differing approaches into the body. The disclosed trans-venous approach disclosed for delivery an occlusion device to an aorto-caval fistula will not be used for delivering closure devices to other locations in the cardiovascular system, such as to close a transapical hole into the left ventricle. In other methods, transarterial, transthoracic, or other approaches can be used to deliver a catheter carrying a radially compressed occlusion device to the passageway. It can be desirable, regardless of the approach, to deliver the occlusion device from the lower pressure side of the passageway, in order to minimize hemorrhaging and other complications. In addition, it can be desirable to orient the occlusion device such that the first end portion is deployed from the delivery catheter into the high pressure side of the passageway prior to deploying the neck portion within the passageway and/or prior to deploying the second end portion into the lower pressure side of the passageway. For example, to close a transapical hole into the left ventricle, the occlusion device can be delivered in a catheter from the outside of the heart, through the hole, and the first end portion can be deployed first into the left ventricle prior to the neck portion and the second end portion (if present) being deployed.

FIGS. 8-12 illustrate an exemplary delivery system for use with an occlusion device as described herein. The delivery system can include an attachment member 300 (FIGS. 8-9) and a delivery shaft 400 (FIG. 10), and can further include other components not illustrated. The attachment member 300 can comprise a non-metallic material, such as a polymeric material or other suitable rigid and strong material. The shaft 400 can comprise a semi-flexible yet semi-rigid material that allows bending to extend through the vasculature to the implantation site, but also allows torque transmission to the attachment device from an operator. The exemplary attachment member 300 has a distal end 302, a proximal end 304, an ovoid guidewire channel 306 extending through the member between the distal and proximal ends, external threads 308 adjacent to the distal end for coupling to the occlusion device, and a proximal socket 310 having flat lateral surfaces 312 and a rounded end surface 314 around the guidewire channel 306. The socket 310 is configured to receive and retain a distal ball 404 of the delivery shaft 400 to provide a pivot joint therebetween.

The delivery shaft 400 includes an elongated proximal shaft portion 402 that extends through a catheter and allows manual control of the delivery system. The shaft portion 402 can be semi-rigid such that is flex and traverse through the veins while still being rigid enough to impart torque and other forces to the occlusion device. The shaft portion is coupled to the distal ball 404 by a narrow neck portion 406 and a tapered shaft end 414. A guidewire channel 408 extends longitudinally through the shaft portion 402, the neck portion 406, and the ball 404. The guidewire channel 408 can have an ovoid shape at least at the distal end proximate the ball 404. The ball 404 can have a rounded surface 410 and two opposing flat surfaces 412 on lateral sides of the ball.

Figure 11:
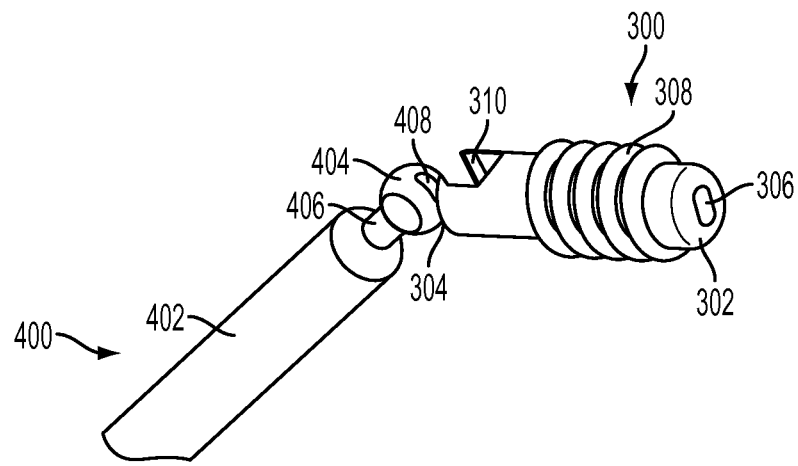
Figure 12:
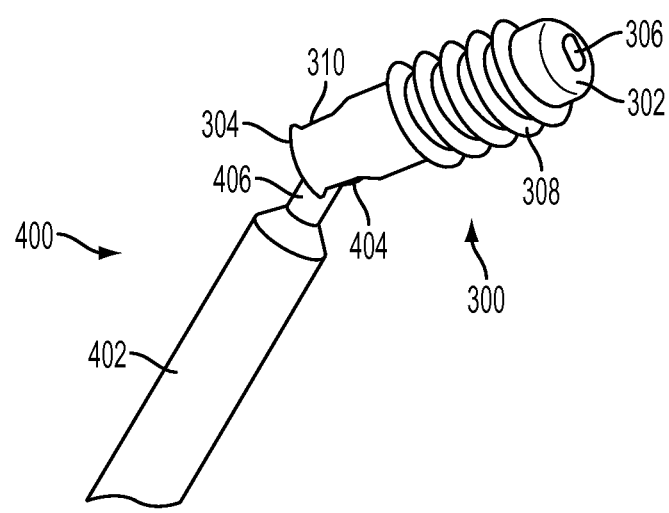

As shown in FIGS. 11 and 12, the ball 404 is positioned within socket 310 such that the rounded surface 410 engages the rounded end surface 314 of the socket and the flat surfaces 412 of the ball contact the flat lateral surfaces 312 of the socket. The proximal end of the socket can extend around the ball 404 and retain the ball in the socket while allowing articulation in the ball joint. The mating flat surfaces 410 and 312 in the ball joint can limit the pivoting motion allowed to a single plane that is parallel to the flat surfaces. The pivot joint can allow the attachment member 300 to pivot in such a plane relative to the longitudinal axis of the delivery shaft, while keeping the attachment member from pivoting out of the plane. The pivot joint can allow the attachment member 300 to pivot to almost any angle in the plane, such as to a right angle relative to the longitudinal axis of the delivery shaft, or more beyond a right angle.

While the pivot joints allows the attachment member to pivot relative to the shaft 400, the ovoid guidewire shafts 306, 408 in each component can be sized such that they allow a guidewire passing through them and across the ball joint at a wide range of pivot angles. The ovoid guidewire channels 306, 408 can have an elongated width extending in the pivot plane to allow a guidewire to shift across the elongated width as the pivot angle changes. This allows the delivery shaft 400 and the guidewire to not distort the final position of the occlusion device before release.

The pivotability of the ball joint allows the delivery device to direct the occlusion device attached to the threads 308 of the attachment member 300 into or across a passageway that is at a transverse angle relative to the longitudinal angle of the vein. As illustrated in FIG. 1F, the delivery shaft 400 or 70 can extend through the vein generally parallel with the longitudinal axis of the vein, while allowing the attachment member 300 or 72 to pivot and extend in the direction of the passageway in order to insert the occlusion device longitudinally across the passageway.

Due to the engaged flat surfaces 312, 410 in the ball joint, the delivery shaft 400 cannot rotate freely around the guidewire relative to the attachment member 300. This allows rotation of the delivery shaft 400 to impart torque across the ball joint to the attachment member 300 in order to unscrew the attachment member from the occlusion device after implantation, or to screw the attachment member back into the occlusion device if desired.

The guidewire channels 306 and 408 in the delivery system can further allow a guidewire to guide the delivery system over the guidewire back to the deployed occlusion device such that the attachment member 300 can be re-attached to the occlusion device, such as for adjusting its position or recapturing it. In other methods, a recapture system can be used to recapture a deployed occlusion device. Such a recapture system can have a central guidewire lumen extending through its length such that it can be introduced over a guidewire that is positioned extending through the deployed occlusion device. The recapture system can be advanced over the guidewire until its distal end reaches the proximal end of the deployed occlusion device, whereupon the recapture system can recapture the deployed occlusion device. The recapture system may include an attachment mechanism (e.g., threads, clamp, etc.) that can attach to the proximal end of the deployed occlusion device and/or a tubular device that can be positioned over and/or receive the occlusion device. For example, the occlusion device can be pulled using the attachment mechanism into a sheath that causes the occlusion device to radially compress and enter into a lumen of the sheath.

In view of the many possible embodiments to which the principles of the disclosed technology may be applied, it should be recognized that the illustrated embodiments are only preferred examples and should not be taken as limiting the scope of the disclosure. Rather, the scope of the disclosure is defined as being at least as broad as the following exemplary claims. We therefore reserve the right to claim at least all that comes within the scope of these exemplary claims.

We claim:

1. An occlusion system for transcatheter closure of a passageway in the cardiovascular system, comprising:

an implant that is resiliently deformable into a radially compressed configuration for transcatheter delivery and radially self-expandable to an implanted configuration;

the implant comprising a proximal end portion, a distal end portion, and an intermediate neck portion between the proximal end portion and the distal end portion;

the implant configured to be implanted across a passageway in the cardiovascular system with the distal end portion positioned at a first end of the passageway, the proximal end portion positioned on a second, opposite end of the passageway, and the neck portion positioned in the passageway;

wherein when implanted, the distal end portion of the implant is radially enlarged relative to the neck portion such that the distal end portion forms a distal skirt that contacts a wall of a cardiovascular chamber or vessel at the first end of the passageway and blocks blood flow from the cardiovascular chamber or vessel into the passageway;

the implant further comprising a longitudinal guidewire channel extending through the proximal end portion, the neck portion, and the distal end portion of the implant, wherein the guidewire channel allows the implant to be delivered over a guidewire and the guidewire channel is configured to be occluded when a guidewire is not present in the guidewire channel;

the occlusion system further comprising a detachable delivery system comprising an attachment member attached to a delivery shaft, wherein the attachment member is detachably couplable to the implant at an attachment location at a venous end of the guidewire channel, and wherein the delivery shaft and attachment member include a guidewire channel extending longitudinally therethrough such that the delivery system and the implant can be advanced over a guidewire extending through the guidewire channels in the delivery shaft, attachment member, and implant;

wherein the delivery shaft terminates in a distal ball joint having flat opposing faces and the central guidewire channel extends entirely through the delivery shaft and through the distal ball joint, and the distal ball joint engages the attachment member such that the delivery shaft pivots in only one plane relative to the attachment member during positioning of the implant, and the delivery shaft is configured to transfer torque to the attachment member when the delivery shaft is rotated for selective attachment and detachment of the attachment member from the implant.

2. The occlusion system of claim 1, wherein the attachment member comprises a threaded portion that screws into the attachment location of the implant and couples the guidewire channels together.

3. The occlusion system of claim 1, wherein the attachment member is pivotable relative to the delivery shaft about a pivot axis that is transverse to a longitudinal axis of the delivery shaft.

4. The occlusion system of claim 1, wherein the first end of the passageway is under higher pressure than the second end of the passageway and the implant comprises a non-metallic liner on a sealing face of the enlarged distal skirt that conforms to the wall of the cardiovascular chamber or vessel at the higher pressure end of the passageway when implanted.

5. The occlusion system of claim 1, wherein the proximal end portion of the implant is radially enlarged relative to the neck portion when the implant is implanted such that the proximal end portion forms an enlarged proximal skirt that contacts a wall of a cardiovascular chamber or vessel at the second end of the passageway.

6. The occlusion system of claim 1, wherein the neck portion of the implant is longitudinally extensible to accommodate variation in distance between the proximal end portion and the distal end portion.

7. The occlusion system of claim 1, wherein the neck portion of the implant is angularly articulable to accommodate non-transverse trajectories of the passageway between the distal end portion and the proximal end portion.

8. The occlusion system of claim 1, wherein the implant comprises elastomeric material in or around the guidewire channel that resiliently seals off of the guidewire channel when a guidewire is not present in the guidewire channel.

9. The occlusion system of claim 1, wherein the neck portion comprises a plurality of circumferential corrugations that are elastically deformable by tensile force applied on the implant to cause the corrugations to pull out and lengthen the neck portion, and wherein the neck portion is configured to change length without substantial change in diameter.

10. The occlusion system of claim 1, wherein the neck portion comprises a woven or braided material having varying weave or braid density that allows the neck portion to lengthen under tensile force applied on the implant, and wherein the neck portion is configured to change length without substantial change in diameter.

* * * * *